United States Patent [19]
Ashraf et al.

[11] Patent Number: 6,121,509
[45] Date of Patent: *Sep. 19, 2000

[54] ABSORBENT POLYMER COMPOSITIONS HAVING HIGH SORPTION CAPACITIES UNDER AN APPLIED PRESSURE AND IMPROVED INTEGRITY WHEN WET

[75] Inventors: Arman Ashraf; Bryn Hird, both of Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/003,918

[22] Filed: Jan. 7, 1998

[51] Int. Cl.[7] .............................. A61F 13/15; A61F 13/20
[52] U.S. Cl. ..................... 604/368; 604/372; 442/301
[58] Field of Search ..................................... 442/301, 414; 604/358, 367, 368, 372, 374, 375; 428/913

[56] References Cited

U.S. PATENT DOCUMENTS

| | | | |
|---|---|---|---|
| Re. 32,649 | 4/1988 | Brandt et al. .......................... | 604/368 |
| 4,625,001 | 11/1986 | Tsubakimoto et al. .................. | 526/88 |
| 4,666,983 | 5/1987 | Tsubakimoto et al. .................. | 525/119 |
| 4,818,598 | 4/1989 | Wong ..................................... | 428/284 |
| 4,834,735 | 5/1989 | Alemanry et al. ...................... | 604/368 |
| 5,274,018 | 12/1993 | Tanaka et al. .......................... | 524/166 |
| 5,384,368 | 1/1995 | Date et al. . | |
| 5,466,731 | 11/1995 | Akers et al. ............................. | 524/52 |
| 5,562,646 | 10/1996 | Goldman et al. ....................... | 604/368 |
| 5,599,335 | 2/1997 | Goldman et al. ....................... | 604/368 |
| 5,669,894 | 9/1997 | Goldman et al. ....................... | 604/368 |

FOREIGN PATENT DOCUMENTS

| | | | |
|---|---|---|---|
| 0 210 756 A2 | 2/1987 | European Pat. Off. ........ | A61L 15/00 |
| 57-35938 | 2/1982 | Japan ............................. | B01J 20/26 |
| 57-45057 | 3/1982 | Japan . | |
| WO 95/22358 | 8/1995 | WIPO ............................ | A61L 15/60 |
| WO 95/26209 | 10/1995 | WIPO . | |
| WO 96/15154 | 5/1996 | WIPO ............................ | C08B 3/14 |
| WO 96/15162 | 5/1996 | WIPO ............................ | C08F 20/06 |
| WO 96/15163 | 5/1996 | WIPO ............................ | C08F 20/56 |
| WO 96/15180 | 5/1996 | WIPO ............................ | C08J 5/02 |
| WO 96/17681 | 6/1996 | WIPO ............................ | B01J 20/00 |
| WO 98/24832 | 6/1998 | WIPO ............................ | C08J 3/075 |

*Primary Examiner*—Daniel Zirker
*Attorney, Agent, or Firm*—Carl J. Roof; Edward J. Milbrada; Mary Catherine Hentz

[57] ABSTRACT

Disclosed in the present application are absorbent materials useful in the containment of body fluids such as urine. In particular, the invention relates to absorbent polymer compositions having excellent absorbency performance properties in terms of absorbent capacity under a confining pressure of 0.7 psi, as well has excellent integrity in the swollen state. The invention further relates to absorbent members comprising these absorbent polymer compositions, and to absorbent articles comprising the absorbent members.

41 Claims, 5 Drawing Sheets

ABSORBENT POLYMER COMPOSITIONS HAVING HIGH SORPTION CAPACITIES UNDER AN APPLIED PRESSURE AND IMPROVED INTEGRITY WHEN WET

TECHNICAL FIELD

This application relates to absorbent polymer compositions which have high sorption capacities under an applied load, and improved integrity in the swollen state. These compositions are particularly useful for absorbing body fluids such as urine and menses. The application also relates to absorbent members comprising these absorbent polymers, and to absorbent articles comprising these absorbent members.

BACKGROUND OF THE INVENTION

The development of highly absorbent articles for use as disposable diapers, adult incontinence pads and briefs, and catamenial products such as sanitary napkins, is the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or members that can acquire and store large quantities of discharged body fluids, in particular urine. In this regard, the use of certain absorbent polymers often referred to as "hydrogels", "superabsorbents", "xerogels" or "hydrocolloids" has been particularly important. See for example, U.S. Pat. No. 3,699,103 (Harper et al.), issued Jun. 13, 1972, and U.S. Pat. No. 3,770,731 (Harmon), issued Jun. 20, 1972, that disclose the use of such materials (hereinafter referred to as "absorbent polymers") in absorbent articles. Indeed, the development of thinner diapers has been the direct consequence of thinner absorbent cores that take advantage of the ability of these absorbent polymers to absorb large quantities of discharged body fluids, typically when used in combination with a fibrous matrix. See for example, U.S. Pat. No. 4,673,402 (Weisman et al.), issued Jun. 16, 1987 and U.S. Pat. No. 4,935,022 (Lash et al.), issued Jun. 19, 1990, that disclose dual-layer core structures comprising a fibrous matrix and absorbent polymers useful in fashioning thin, compact, nonbulky diapers.

These absorbent polymers are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylene-bisacrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-swellable. These lightly crosslinked absorbent polymers contain a multiplicity of carboxyl groups attached to the polymer backbone. These carboxyl groups generate an osmotic driving force for the absorption of body fluids by the crosslinked polymer network. Absorbent polymers can also be made by polymerizing unsaturated amines or derivatives thereof in the presence of relatively small amounts of di- or poly-functional monomers, in an analogous fashion.

The degree of cross-linking of these absorbent polymers is an important factor in establishing their absorbent capacity and gel strength. Absorbent polymers useful as absorbents in absorbent members and articles such as disposable diapers need to have adequately high sorption capacity, as well as adequately high gel strength. Sorption capacity needs to be sufficiently high to enable the absorbent polymer to absorb significant amounts of the aqueous body fluids encountered during use of the absorbent article. Gel strength relates to the tendency of the swollen polymer particles to deform under an applied stress, and needs to be such that the particles do not deform and fill the capillary void spaces in the absorbent member or article to an unacceptable degree, thereby inhibiting the rate of fluid uptake or the fluid distribution by the member or article. In general, increasing gel strength will result in an increase in the permeability of a zone or layer comprising swollen absorbent polymer. However, this typically also reduces the absorbent capacity of the gel undesirably. See, for example, U.S. Pat. No. 4,654,039 (Brandt et al.), issued Mar. 31, 1987 (reissued Apr. 19, 1988 as U.S. Reissue Pat. No. 32,649) and U.S. Pat. No. 4,834,735 (Alemany et al.), issued May 30, 1989.

Many absorbent polymers can exhibit gel blocking under certain conditions. "Gel blocking" occurs when particles of the absorbent polymer deform so as to fill the capillary void spaces in the absorbent member or article to an unacceptable degree, thereby inhibiting the rate of fluid uptake or the distribution of fluid by the member/article. Once gel-blocking occurs, further fluid uptake or distribution takes place via a very slow diffusion process. In practical terms, this means that gel-blocking can substantially impede the distribution of fluids to relatively dry zones or regions in the absorbent member or article. Leakage from the absorbent article can take place well before the particles of absorbent polymer in the absorbent article are fully saturated or before the fluid can diffuse or wick past the "blocking" particles into the rest of the absorbent article. See U.S. Pat. No. 4,834,735 (Alemany et al), issued May 30, 1989

This gel blocking phenomenon has typically necessitated the use of a fibrous matrix in which are dispersed the particles of absorbent polymer. This fibrous matrix keeps the particles of absorbent polymer separated from one another and provides a capillary structure that allows fluid to reach the absorbent polymer located in regions remote from the initial fluid discharge point. See U.S. Pat. No. 4,834,735 (Alemany et al), issued May 30, 1989. However, dispersing the absorbent polymer in a fibrous matrix at relatively low concentrations in order to minimize or avoid gel blocking can significantly increase the bulkiness of the absorbent article or lower the overall fluid storage capacity of thinner absorbent structures. Using low concentrations of absorbent polymers limits somewhat the real advantage of these materials, i.e. their ability to absorb and retain large quantities of body fluids per given volume.

Another factor which affects the transport of fluid in an absorbent member is the integrity of the region or regions that comprise these particles of absorbent polymer. Such region or regions having the high concentration of absorbent polymer should have sufficient integrity in a partially wet and/or wetted state such that the physical continuity (and thus the capability of acquiring and transporting fluid into and through contiguous interstitial voids/capillaries) of the absorbent member is not substantially disrupted or altered when subjected to normal use conditions. During normal use, absorbent cores in absorbent articles are typically subjected to tensional and torsional forces of varying intensity and direction. These tensional and torsional forces include bunching in the crotch area, stretching and twisting forces as the person wearing the absorbent article walks, squats, bends, and the like. If wet integrity is inadequate, these tensional and torsional forces can potentially cause a substantial alteration and/or disruption in the physical continuity of the absorbent member such that its capability of acquiring and transporting fluids into and through the contiguous voids and capillaries is degraded. The layer comprising absorbent polymer can be partially separated, be fully separated, have gaps introduced, have areas that are significantly thinned, and/or be broken up into a plurality of significantly smaller segments.

The integrity of a swollen layer of the absorbent polymer can be increased by various techniques . For example, the particles of absorbent polymer may be coated with a second polymer that has a strong affinity for the polymer comprising the absorbent particles. When aqueous fluid is introduced to such a system, this second polymer can bridge between the absorbent polymer particles to form a three-dimensional network of particles bound together by polymer chains. This technique is described in greater detail, for example, in U.S. Pat. No. 5,382,610, filed Jan. 17, 1995, in which conventional absorbent polymer particles comprising poly(acrylic acid) are coated with polyethylenimine to yield swollen polymer matrices with good integrity. However, although the integrity of the swollen polymer can be increased by this technique, the absorbent capacity of the system under normal use conditions is generally depressed. Furthermore, the integrity of the swollen polymer matrix tends to deteriorate with time, as the uncrosslinked polymer which binds the particles together is able to diffuse away from the surfaces of the polymer particles.

Accordingly, it would be desirable to provide an absorbent polymer composition capable of absorbing a large quantity of a synthetic urine solution. It would also be desirable that the region or regions in the absorbent member comprising these absorbent polymers have sufficient integrity in a partially wet and/or highly swollen state such that the physical continuity (and thus the capability of acquiring and transporting fluid through contiguous interstitial voids/capillaries) is not substantially disrupted or altered, even when subjected to normal use conditions.

SUMMARY OF THE INVENTION

The present invention relates to absorbent materials useful in the containment of body fluids such as urine. In particular, the invention relates to absorbent polymers having very high absorbent capacities under confining pressures of 0.7 psi and/or 1.4 psi, wherein the absorbent polymer provides high gel bed integrity, particularly in the swollen state upon exposure to synthetic urine solution.

In one aspect, the invention relates to an absorbent polymer composition having (i) a Performance under Pressure (PUP) capacity of at least about 39 g/g under a confining pressure of 0.7 psi (4.8 kPa) after 4 hours and (ii) a Ball Burst Strength (BBS) value of at least about 50 grams force (gf). (The methods for measuring PUP capacity and BBS are described below). In another aspect, the present invention relates to an absorbent polymer composition having a PUP capacity of at least about 36 g/g under a confining pressure of 0.7 psi after 4 hours and (ii) a BBS value of at least about 100 gf. In yet another aspect, the present invention relates to an absorbent polymer composition having a PUP capacity of at least about 33 g/g under a confining pressure of 0.7 psi after 4 hours and (ii) a BBS value of at least about 150 gf. In still another aspect, the present invention relates to an absorbent polymer composition having a PUP capacity of at least about 30 g/g under a confining pressure of 0.7 psi after 4 hours and (ii) a BBS value of at least about 200 gf. As used herein, the term "after" means immediately after.

In a preferred embodiment, the invention relates to a composition comprising cation-exchange absorbent polymers that contain weak-acid groups in their un-neutralized form, and anion-exchange absorbent polymers that contain weak-base groups in their un-neutralized form, wherein the mixture exhibits high absorbence of a synthetic urine solution under PUP-absorption conditions and relatively high wet integrity. This mixture is referred to herein as a "mixed-bed ion-exchange absorbent polymer composition." Such mixed-bed ion-exchange absorbent polymer compositions will exhibit at least one of the PUP/BBS capacities discussed above.

The invention also relates to absorbent members comprising the above-described absorbent polymer composition, and to absorbent articles comprising such absorbent members.

DETAILED DESCRIPTION OF THE INVENTION

A. Definitions

Figure 1:
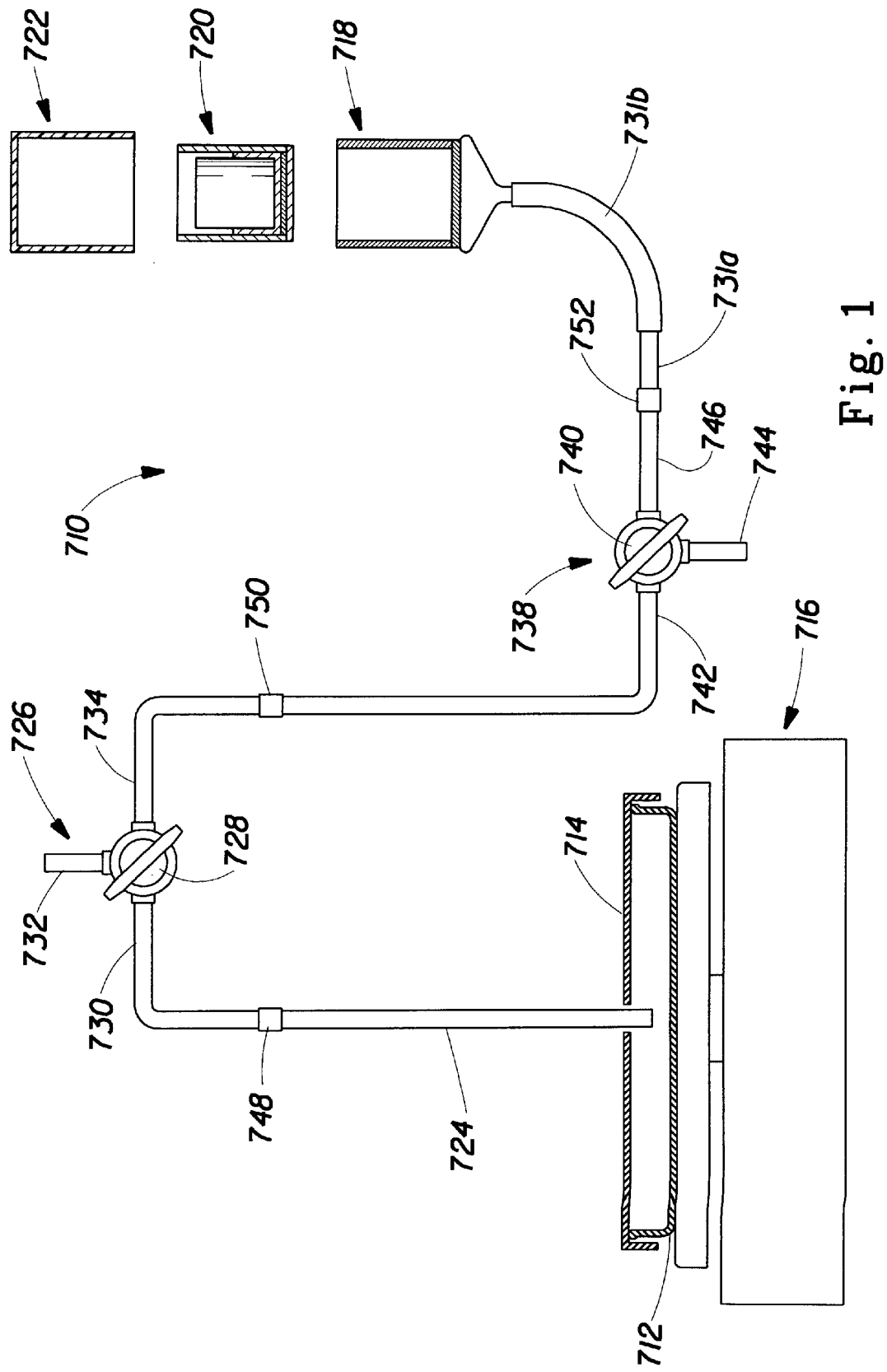
FIG. 1 represents a schematic view of an apparatus for measuring the Performance Under Pressure (PUP) capacity of absorbent polymers.
Figure 2:
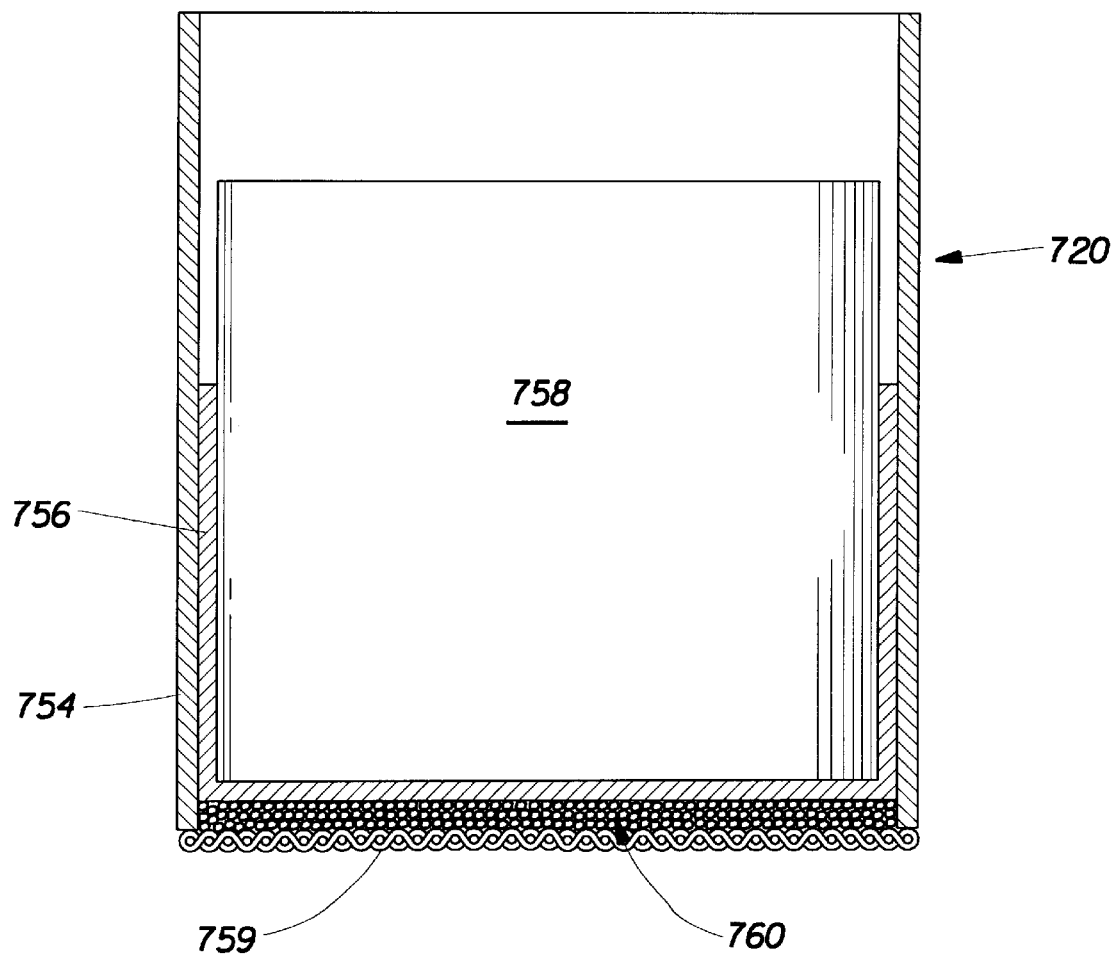
FIG. 2 represents an enlarged sectional view of the piston/cylinder assembly shown in FIG. 1.

As used herein, the term "body fluids" includes urine, blood, menses and vaginal discharges.

As used herein, the term "synthetic urine solution" refers to an aqueous solution prepared by dissolving 2.0 g KCl, 2.0 g $Na_2SO_4$, 0.85 g $NH_4H_2PO_4$, 0.15 g $(NH_4)_2HPO_4$, 0.25 g $CaCl_2.2H_2O$, and 0.50 g $MgCl_2.6H_2O$ in distilled water to yield one litre of solution.

As used herein, the term "ion-exchange capacity" refers to the theoretical or calculated ion-exchange capacity of the polymer or polymers in milliequivalents per gram assuming that each unneutralized acid or base group becomes neutralized in the ion-exchange process.

As used herein, the term "absorbent polymer" refers to a polymer which is capable of absorbing within the polymer at least 10 times its weight in deionized water, allowing for adjustment of the pH of the system.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members. The improved absorbent polymer compositions described herein are particularly useful in absorbent members whose primary function is the storage of aqueous body fluids. However, these compositions may also be present in other absorbent members.

As used herein, the terms "region(s)" or "zone(s)" refer to portions or sections, in a macroscopic sense, of an absorbent member.

As use herein, the term "layer" refers to a portion of an absorbent article whose primary dimensions are along its length and width. It should be understood that the term layer is not necessarily limited to single layers or sheets of material. Thus the layer can be comprised of laminates or combinations of several sheets or webs of the requisite type of materials. Accordingly, the term "layer" includes the terms "layers" and "layered."

As used herein, the term "comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

All publications and references referred to herein are incorporated by reference, at least to the extent they are consistent with the terms and definitions of the present disclosure.

B. Absorbent Polymer Compositions

The present invention relates, in part, to absorbent polymer compositions that exhibit very high absorbency of synthetic urine solution under an applied load, as well as good integrity in the swollen state. The absorbent polymer compositions of the present invention are preferably in the form of a mixed-bed ion-exchange composition which comprises an anion-exchange absorbent polymer and a cation-exchange absorbent polymer. These preferred mixed-bed ion-exchange compositions are described in detail below.

1. Mixed-Bed Ion-Exchange Absorbent Polymers a. Chemical Composition (i) Anion-Exchange Absorbent Polymers The anion-exchange absorbent polymer(s) containing weak-base groups include a variety of water-insoluble, but water-swellable polymers. These are typically lightly crosslinked polymers which contain a multiplicity of base functional groups, such as primary, secondary and/or tertiary amines, or phosphines. Examples of polymers suitable for use herein include those which are prepared from polymerizable monomers which contain base groups, or groups which can be converted to base groups after polymerization. Thus, such monomers include those which contain primary, secondary or tertiary amines, or phosphines. Representative monomers include, but are not limited to, ethylenimine (aziridine), allylamine, diallylamine, 4-aminobutene, alkyl oxazolines, vinylformamide, 5-aminopentene, carbodiimides, formaldazine, melamine, and the like, as well as their secondary or tertiary amine derivatives.

Some monomers which do not contain base groups can also be included, usually in minor amounts, in preparing the anion-exchange absorbent polymers herein. The absorbent polymers described herein can be homopolymers, copolymers (including terpolymers and higher order copolymers), or mixtures (blends) of different homopolymers or copolymers. The polymers may also be random, graft, or block copolymers, and may have linear or branched architectures.

The polymers are rendered water-insoluble, but water-swellable, by a relatively low degree of crosslinking. This may be achieved by including the appropriate amount of a suitable crosslinking monomer during the polymerization reaction. Examples of crosslinking monomers include N,N'-methylenebisacrylamide, ethylene glycol di(meth)acrylate, trimethylolpropane tri(meth)acrylate, triallylamine, diaziridine compounds, and the like. Alternatively, the polymers can be crosslinked after polymerization by reaction with a suitable crosslinking agent such as di- or poly-halogenated compounds and/or di- or poly-epoxy compounds. Examples include diiodopropane, dichloropropane, ethylene glycol diglycidyl ether, and the like. The crosslinks may be homogeneously distributed throughout the gel particle, or may be preferentially concentrated at or near the surface of the particle.

While the anion-exchange absorbent polymer is preferably of one type (i.e., homogeneous), mixtures of anion-exchange polymers can also be used in the present invention. For example, mixtures of crosslinked polyethylenimine and crosslinked polyallylamine can be used in the present invention.

When used as part of a mixed-bed ion-exchange composition, the anion-exchange absorbent polymer starts off from about 50% to about 100%, preferably about 80% to about 100%, more preferably from about 90% to about 100%, in the un-neutralized base form.

In order to maximize the ion-exchange capacity of the mixed-bed ion-exchange absorbent polymer composition, it is desirable that the absorbent polymer have a high ion-exchange capacity per gram of dry polymer. Thus, it is preferred that the ion-exchange capacity of the anion-exchange absorbent polymer component is at least about 10 meq/g, more preferably at least about 15 meq/g, and most preferably at least about 20 meq/g.

(ii) Cation-Exchange Absorbent Polymers

Absorbent polymers useful as cation exchanger(s) typically have a multiplicity of acid functional groups such as carboxylic acid groups. Examples of cation-exchange polymers suitable for use herein include those which are prepared from polymerizable, acid-containing monomers, or monomers containing functional groups which can be converted to acid groups after polymerization. Thus, such monomers include olefinically unsaturated carboxylic acids and anhydrides, and mixtures thereof. The cation-exchange polymers can also comprise polymers that are not prepared from olefinically unsaturated monomers. Examples of such polymers include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247,068, issued Sep. 21, 1993 to Donachy et al., which is incorporated herein by reference.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and anhydride monomers include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, β-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferred cation-exchange absorbent polymers contain carboxyl groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the foregoing copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the cation-exchange absorbent polymers are slightly network crosslinked polymers of polyacrylic acids and starch derivatives thereof. Network crosslinking renders the polymer substantially water-insoluble and, in part, determines the absorptive capacity and extractable polymer content characteristics of the absorbent polymers. Processes for network crosslinking these polymers and typical network crosslinking agents are described in greater detail in U.S. Pat. No. 4,076,663.

While the cation-exchange absorbent polymer is preferably of one type (i.e., homogeneous), mixtures of cation-exchange polymers can also be used in the present invention. For example, mixtures of starch-acrylic acid graft copolymers and slightly network crosslinked polymers of polyacrylic acid can be used in the present invention.

When used as part of a mixed-bed ion-exchange composition, the cation-exchange absorbent polymer starts off from about 50% to about 100%, preferably about 80% to about 100%, more preferably from about 90% to about 100%, in the un-neutralized acid form.

In order to maximize the ion-exchange capacity of the mixed-bed ion-exchange absorbent polymer composition, it is desirable that the cation-exchange absorbent polymer has a high ion-exchange capacity per gram of dry polymer. Thus it is preferred that the ion-exchange capacity of the cation-exchange absorbent polymer component is at least about 4 meq/g, more preferably at least about 8 meq/g, even more preferably at least about 10 meq/g, and most preferably at least about 13 meq/g.

(iii) Composition and Common Material Properties

The equivalents of anionic and cationic exchange capacity may be equal or different in the mixed-bed ion-exchange absorbent polymer composition. For example, it may be desirable to have somewhat more equivalents of anionic or cationic ion-exchange absorbent polymer, e.g., to compensate for differences in pK, to compensate for differences in neutralization, to alter the pH of (for example to acidify) the ion-exchanged urine, etc.

Mixed-bed ion-exchange absorbent polymer compositions in high-concentration absorbent cores cannot rely on solution flow, stirring, etc. to help transport ions between particles and accelerate the rate of ion exchange. Thus it is desirable to have particle morphologies suitable for promoting fast ion-exchange kinetics. Desirable morphologies include (i) mixed-bed aggregates of high-surface-area (e.g., small and/or porous) particles with a broad or narrow particle size distribution, (ii) particles of, e.g., the anion-exchange absorbent polymer that contain within smaller discontinuous domains of e.g., the cation-exchange absorbent polymer, and (iii) particles that contain bicontinuous domains of both anion- and cation-exchange absorbent polymers.

The absorbent polymers can also comprise mixtures with low levels of one or more additives, such as, e.g., powdered silica, surfactants, glues, binders, and the like. The components in this mixture can be physically and/or chemically associated in a form such that the absorbent polymer component and the non-absorbent-polymer additive are not readily physically separable. The absorbent polymers can be essentially non-porous (i.e., no internal porosity) or have substantial internal porosity. In the mixed-bed absorbent polymer composition, the absorbent polymer of one type can have a higher crosslink density than the absorbent polymer of the other type.

For particles of absorbent polymers useful in the present invention, the particles will generally range in size from about 1 to about 2000 microns, more preferably from about 20 to about 1000 microns. The mass median particle size will generally be from about 20 to about 1500 microns, more preferably from about 50 microns to about 1000 microns, and even more preferably from about 100 to about 800 microns.

An important characteristic of absorbent polymers useful in the present invention is the level of extractables present in the polymer itself. See U.S. Pat. No. 4,654,039 (Brandt et al.), issued Mar. 31, 1987 (reissued Apr. 19, 1988 as U.S. Reissue Pat. No. 32,649), the disclosure of each of which is incorporated herein by reference. Many absorbent polymers contain significant levels of extractable polymer material which can be leached out of the swollen polymer matrix by body fluids (e.g., urine) during the time period that such body fluids remain in contact with the absorbent polymer. It is believed such polymer material extracted by body fluid in this manner can alter both the chemical and physical characteristics of the body fluid to the extent that the fluid is more slowly absorbed and more poorly held by the absorbent polymer in the absorbent article. It is also believed that extractable polymer is particularly deleterious in mixed-bed ion-exchange absorbent polymer systems because soluble polymer will tend to migrate to gel particles comprised of oppositely charged polymer. The two polymers will self-neutralize, thereby reducing the ion-exchange capacity of the system. Because extractable polymer effectively comprises a polyvalent counterion to the oppositely charged polymer, it can also form ionic crosslinks which inhibit the ability of the gel to swell.

Accordingly, for absorbent polymers of the present invention, it is preferred that the level of extractable polymer be about 15% or less, more preferably about 10% or less, and most preferably about 7% or less, of the total polymer.

b. Physical Properties (i) Performance Under Pressure (PUP) and Ball Burst Strength (BBS)

Measurement of the Demand Wettability or Gravimetric Absorbence can provide information on the ability of a high concentration zone or layer of the absorbent polymer to absorb body fluids under usage pressures. See, for example, U.S. Pat. No. 5,562,646 (Goldman et al.) issued Oct. 8, 1996 and U.S. Pat. No. 5,599,335 (Goldman et al.) issued Feb. 4, 1997 where Demand Wettability or Gravimetric Absorbence is referred to as Performance Under Pressure (PUP). In a PUP measurement, an initially-dry absorbent polymer composition at 100% concentration is positioned in a piston/cylinder apparatus (where the bottom of the cylinder is permeable to solution, but impermeable to the absorbent polymer) under a mechanical confining pressure and is allowed to absorb synthetic urine solution under demand-absorbency conditions at zero hydrostatic suction and high mechanical pressure. The "PUP" capacity is defined as the g/g absorption of synthetic urine solution by a $0.032$ g/cm$^2$ layer of the absorbent polymer, while being confined under a specific applied pressure for a particular time period. The method for determining PUP capacities may be modified to run for various periods of time, and under various desired confining pressures, in order to simulate particular in-use conditions more closely. The method for determining PUP capacities of absorbent polymers is described in detail in the Test Methods section below. A high PUP capacity is a critically important property for an absorbent polymer when it is used at high concentrations in an absorbent member.

Usage pressures exerted on the absorbent polymers include both mechanical pressures (e.g., exerted by the weight and motions of the user, taping forces, etc.) and capillary pressures (e.g., the capillary desorption pressure of the acquisition component(s) in the absorbent core that temporarily hold fluid before it is absorbed by the absorbent polymer.) It is believed that a total pressure of about 0.7 psi (4.8 kPa) is reflective of the sum of these pressures on the absorbent polymer composition as it absorbs body fluids under usage conditions. However, both higher and lower pressures can also be experienced by the absorbent polymer composition under usage conditions.

Another important factor which affects the transport of fluid in an absorbent member is the integrity of the region or regions that comprise these polymers. Such region or regions having the high concentration of absorbent polymer should have sufficient integrity in a partially wet and/or wetted state such that the physical continuity (and thus the capability of acquiring and transporting fluid into and through contiguous interstitial voids/capillaries) of the absorbent member is not substantially disrupted or altered when subjected to normal use conditions. In addition to the above mechanical and capillary pressures experienced by the absorbent polymer composition, the layer comprising the absorbent polymer composition is typically subjected to tensional and torsional forces of varying intensity and direction during the normal use of an absorbent article. These tensional and torsional forces include bunching in the crotch area, stretching and twisting forces as the person wearing the absorbent article walks, squats, bends, and the like. If wet integrity is inadequate, these tensional and torsional forces can potentially cause a substantial alteration and/or disruption in the physical continuity of the absorbent member such that its capability of acquiring and transporting fluids into and through the contiguous voids and capillaries is degraded. The layer comprising absorbent polymer can be partially separated, be fully separated, have gaps introduced, have areas that are significantly thinned, and/or be broken up into a plurality of significantly smaller segments. Such alteration can impair the ability of the layer comprising absorbent polymer to acquire and transport fluid, thereby reducing the overall efficacy of the absorbent polymer in the absorbent article.

The Ball Burst Strength (BBS) of a swollen layer of the absorbent polymer composition can provide a measure of the integrity of the layer of the absorbent polymer composition in the swollen state. The BBS is the force (peak load, in grams force) required to rupture a layer of an absorbent polymer composition that is swollen in synthetic urine solution, under specific conditions. In a Ball Burst Strength measurement, a 1.0 g sample of the absorbent polymer composition is allowed to absorb 30 mL of synthetic urine solution to form a swollen gel layer. The force required to rupture the layer with a ball-shaped stainless steel probe is the Ball Burst Strength of the material. The method for determining Ball Burst Strengths of absorbent polymers is described in detail in the Test Methods section below. As is discussed above, a relatively high Ball Burst Strength indicates good integrity of a layer comprising a high concentration of absorbent polymer.

The absorbent polymer compositions of the present invention are described in terms of their ability to absorb synthetic urine under a confining pressure of 0.7 psi as well as their ability to exhibit relatively high integrity in the swollen state. In this regard, the invention relates to an absorbent polymer composition having a Performance Under Pressure (PUP) capacity in synthetic urine solution of at least about 39 g/g under a confining pressure of 0.7 psi after 4 hours and a Ball Burst Strength (BBS) of at least about 50 gf. Preferably, the polymer composition will have a PUP capacity in synthetic urine solution of at least about 41 g/g, more preferably at least about 43 g/g and most preferably at least about 44 g/g after 4 hours, under a confining pressure of 0.7 psi; and a BBS of at least about 50 gf. Typically, in addition to the BBS requirement, the polymer composition will have a PUP capacity of from about 39 g/g to about 58 g/g, more typically from about 41 g/g to about 55 g/g, and still more typically from about 43 g/g to about 50 g/g, under a confining pressure of 0.7 psi.

In another aspect, the absorbent polymer composition will have a PUP capacity in synthetic urine solution of at least about 36 g/g under a confining pressure of 0.7 psi after 4 hours and a BBS value of at least about 100 gf. Preferably, the polymer composition will have PUP capacity of at least about 38 g/g, more preferably at least about 40 g/g and most preferably at least about 42 g/g after 4 hours, under a confining pressure of 0.7 psi.; and a BBS value of at least about 100 gf. Typically, in addition of a BBS value of at least about 100 gf, the polymer composition will have a PUP capacity of from about 36 g/g to about 58 g/g, more typically from about 38 g/g to about 55 g/g, still more typically from about 40 g/g to about 50 g/g, and still more typically from about 42 g/g to about 50 g/g after 4 hours, under a confining pressure of 0.7 psi.

In still another similar aspect, the absorbent polymer composition will have a PUP capacity of at least about 33 g/g under a confining pressure of 0.7 psi after 4 hours and a BBS value of at least about 150 gf. Preferably, the polymer composition will have PUP capacity of at least about 35 g/g, more preferably at least about 37 g/g and most preferably at least about 40 g/g after 4 hours, under a confining pressure of 0.7 psi.; and a BBS value of at least about 150 gf. Typically, in addition to having a BBS value of at least about 150 gf, the polymer composition will have a PUP capacity of from about 33 g/g to about 58 g/g, more typically from about 35 g/g to about 55 g/g, still more typically from about 37 g/g to about 50 g/g, and still more typically from about 40 g/g to about 50 g/g after 4 hours, under a confining pressure of 0.7 psi.

In yet another aspect, the absorbent polymer composition will have a PUP capacity of at least about 30 g/g under a confining pressure of 0.7 psi after 4 hours and a BBS value of at least about 200 gf. Preferably, the polymer composition will have PUP capacity of at least about 32 g/g, more preferably at least about 34 g/g and most preferably at least about 37 g/g after 4 hours, under a confining pressure of 0.7 psi.; and a BBS value of at least about 200 gf. Typically, in addition to having a BBS value of at least about 200 gf, the polymer composition will have a PUP capacity of from about 30 g/g to about 58 g/g, more typically from about 32 g/g to about 55 g/g, still more typically from about 34 g/g to about 50 g/g, and still more typically from about 37 g/g to about 50 g/g after 4 hours, under a confining pressure of 0.7 psi.

As indicated above, the absorbent polymer compositions of the present invention have a BBS value of at least about 50 gf to at least about 200 gf, depending on the sorption capacity of the composition. Regardless of the sorption capacity under pressure, the BBS values will typically range from about 50 to about 1000 gf, more typically from about 100 to about 800 gf, still more typically from about 150 to about 400 gf and most typically from about 200 to about 300 gf.

Good integrity of the zone or layer comprising absorbent polymer can be achieved according to the present invention by various designs, configurations, compositions, etc., in the absorbent member having the high concentration of absorbent polymer, the other components in the absorbent core (e.g., fluid acquisition members), the other components in the absorbent article (e.g., the topsheet and/or backsheet), or any combination of these components. See U.S. Pat. No. 5,562,646, issued Oct. 8, 1996 to Goldman et al.

In preferred mixed-bed ionic-exchange systems, the cation-exchange component and the anion-exchange component tend to adhere to one another. Without being bound by theory, this is believed to be due to the oppositely charged polyions and or acid/base species at the surfaces of the polymer gel particles which are inherently attracted to oppositely charged species in adjacent particles. This causes a three-dimensional network of adhering polymer particles to be established in the hydrogel zone or layer, thereby greatly enhancing the integrity of this zone or layer.

In this regard, the absorbent polymer compositions of the present invention will have BBS values as described above.

(ii) Permeability of the Zone or Layer Comprising Absorbent Polymer

Another relevant property of zones or layers comprising absorbent polymers is their permeability to fluid. In an absorbent member or article, this directly affects the ability of a material, such as the layer comprising the swollen absorbent polymer to transport body fluids away from the acquisition region at an acceptable rate. Permeability/flow conductivity can be defined in terms of Saline Flow Conductivity (SFC), which is a measure of the ability of a material to transport saline fluid. An absorbent polymer is deemed to have desirable permeability properties if its SFC value is at least about $30 \times 10^{-7}$ cm$^3$ sec/g. A method for measuring saline flow conductivity is described in U.S. Pat. No. 5,562,646 (Goldman et al.) issued Oct. 8, 1996. This method is modified to account for gel bed deswelling during the measurement of mixed-bed ion-exchange absorbent polymers, as described in the Test Methods section below. Without being bound by theory, it is believed that during the SFC measurement of mixed-bed ion-exchange absorbent polymers, the polymer sample continues to exchange ions from the saline solution. Ultimately, the ion-exchange capacity of the absorbent polymer is exceeded, and the ionic strength of the solution surrounding the swollen polymer increases, resulting in some deswelling of the gel bed. The amount of fluid that is expressed from the gel as a result of this deswelling is small compared to the amount of fluid which flows through the gel bed during the SFC measurement. Because the final thickness of the gel bed is significantly less than the initial thickness, the final thickness of the gel bed is used to calculate SFC values. Using the final thickness of the gel bed in the calculation provides the minimum SFC attained during the measurement. Using the initial or an intermediate thickness of the gel bed will provide even higher SFC values.

The absorbent polymer compositions of the present invention will preferably, though not necessarily, have an SFC value of at least about $30 \times 10^{-7}$ cm$^3$ sec/g, more preferably at least about $50 \times 10^{-7}$ cm$^3$ sec/g, and still more preferably at least about $70 \times 10^{-7}$ cm$^3$ sec/g. Typically, the absorbent polymers of the present invention will have an SFC value from about 30 to about $100 \times 10^{-7}$ cm$^3$ sec/g, more typically from about 50 to about $90 \times 10^{-7}$ cm$^3$ sec/g, and still more typically from about 70 to about $80 \times 10^{-7}$ cm$^3$ sec/g (iii) Porosity of the Zone or Layer Comprising Absorbent Polymer Another characteristic of the absorbent polymers of the present invention is the openness or porosity of the zone or layer comprising the absorbent polymers when the polymers are swollen in body fluids under a confining pressure. It is believed that when the absorbent polymers useful herein are present at high concentrations in an absorbent member or absorbent article and then swell under usage pressures, the boundaries of the particles come into contact, and interstitial voids in this high-concentration region become generally bounded by swollen polymer. When this occurs, it is believed the openness or porosity properties of this region are generally reflective of the porosity of the zone or layer formed from the swollen absorbent polymer alone. As used herein, the term "porosity" means the fractional volume (dimensionless) that is not occupied by solid material. See J. M. Coulson et al., Chemical Engineering Vol. 2, 3$^{rd}$ Edition, Pergamon Press, 1978, p. 126.

Porosity is an effective measure of the ability of the zone or layer comprising swollen absorbent polymer to remain open so as to be able to acquire and distribute body fluids under usage pressures. It is believed that increasing the porosity of swollen high-concentration regions can provide superior absorption and fluid handling properties for the absorbent core, thus decreasing incidents of leakage, especially at high fluid loadings. Desirably the porosity of the zone or layer comprising swollen absorbent polymer approaches or even exceeds the porosity of conventional acquisition/distribution materials such as wood-pulp fluff. See U.S. Pat. No. 5,562,646, issued Oct. 8, 1996 to Goldman et al.

c. Methods for Making Absorbent Polymers

The absorbent polymers useful in the present invention can be formed by any polymerization and/or crosslinking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference.

Polymerization methods to prepare ion-exchange polymers useful in the present invention can include free radical, ring-opening, condensation, anionic, cationic, or irradiation techniques. The polymer may be prepared in the neutralized, partially neutralized, or un-neutralized form, even though the desired product is un-neutralized. The absorbent polymer may be prepared using a homogeneous solution polymerization process, or by multi-phase polymerization techniques such as inverse emulsion or suspension polymerization procedures.

Crosslinking can be effected during polymerization by incorporation of suitable crosslinking monomers. Alternatively, the polymers can be crosslinked after polymerization by reaction with a suitable reactive crosslinking agents. Surface crosslinking of the initially formed polymers is a preferred process for obtaining absorbent polymers having relatively high PUP capacity, porosity and permeability. Without being bound by theory, it is believed that surface crosslinking increases the resistance to deformation of the surfaces of swollen absorbent polymer particles, thus reducing the degree of contact between neighboring polymer particles when the swollen particles are deformed under an external pressure. Surface crosslinked absorbent polymers have a higher level of crosslinking in the vicinity of the surface than in the interior. As used herein, "surface" describes the outer-facing boundaries of the particle. For porous absorbent polymers (e.g., porous particles, etc.), exposed internal boundaries can also be included. By a higher level of crosslinking at the surface, it is meant that the level of functional crosslinks for the absorbent polymer in the vicinity of the surface is generally higher than the level of functional crosslinks for the polymer in the interior. The gradation in crosslinking from surface to interior can vary, both in depth and profile.

A number of processes for introducing surface crosslinks are disclosed in the art. Suitable methods for surface crosslinking include those where (i) a di- or poly-functional reagent(s) capable of reacting with existing functional groups within the absorbent polymer is applied to the surface of the absorbent polymer; (ii) a di- or poly-functional reagent that is capable of reacting with other added reagents and possibly existing functional groups within the absorbent polymer such as to increase the level of crosslinking at the surface is applied to the surface (e.g., the addition of monomer plus crosslinker and the initiation of a second polymerization reaction); (iii) no additional poly-functional reagents are added, but additional reaction(s) is induced amongst existing components within the absorbent polymer either during or after the primary polymerization process such as to generate a higher level of crosslinking at or near the surface (e.g., suspension polymerization processes wherein the crosslinker is inherently present at higher levels near the surface); and (iv) other materials are added to the surface such as to induce a higher level of crosslinking or otherwise reduce the surface deformability of the resultant hydrogel. Suitable general methods for carrying out surface crosslinking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164, 459 (Kimura et al.), issued Nov. 17, 1992; published German patent application 4,020,780 (Dahmen), published Aug. 29, 1991; and published European patent application 509, 708 (Gartner), published Oct. 21, 1992; all of which are incorporated herein by reference. For cationic absorbent polymers, suitable di- or poly-functional crosslinking reagents include di/poly-haloalkanes, di/poly-epoxides, di/poly-acid chlorides, di/poly-tosyl, alkanes di/poly-aldehydes, di/poly-acids, and the like.

C. Test Methods

1. Performance Under Pressure (PUP) Capacity

This test is based on the method described in U.S. Pat. No. 5,599,335 (Goldman et al.) issued Feb. 4, 1997. The test determines the amount of synthetic urine solution absorbed by absorbent polymers (including mixed-bed ion-exchange absorbent polymer compositions) that are laterally confined in a piston/cylinder assembly under a confining pressure, e.g. of 0.7 psi or 1.4 psi. The objective of the test is to assess the ability of the absorbent polymer to absorb body fluids over a period of time comparable to the duration of use (e.g., overnight) of articles comprising the absorbent polymer compositions (e.g., 1, 2, 4, 8, or 16 hours), when the polymers are present at high concentrations in an absorbent member and exposed to usage pressures. Usage pressures against which absorbent polymer are required to absorb fluid include mechanical pressures resulting from the weight and/or motions of the wearer, mechanical pressures resulting from elastics and fastening systems, and the hydrostatic desorption pressures of adjacent layers and/or members.

The test fluid for the PUP capacity test is synthetic urine solution. This fluid is absorbed by the absorbent polymers under demand absorption conditions at near-zero hydrostatic pressure.

A suitable apparatus for this test is shown in FIG. 1. At one end of this apparatus is a fluid reservoir 712 (such as a petri dish) having a cover 714. Reservoir 712 rests on an analytical balance indicated generally as 716. The other end of apparatus 710 is a fritted funnel indicated generally as 718, a piston/cylinder assembly indicated generally as 720 that fits inside funnel 718, and cylindrical plastic fritted funnel cover indicated generally as 722 that fits over funnel 718 and is open at the bottom and closed at the top, the top having a pinhole. Apparatus 710 has a system for conveying fluid in either direction that consists of sections glass tubing indicated as 724 and 731a, flexible plastic tubing (e.g., ¼ inch i.d. and ⅜ inch o.d. Tygon® tubing) indicated as 731b, stopcock assemblies 726 and 738 and Teflon® connectors 748, 750 and 752 to connect glass tubing 724 and 731a and stopcock assemblies 726 and 738. Stopcock assembly 726 consists of a 3-way valve 728, glass capillary tubing 730 and 734 in the main fluid system, and a section of glass capillary tubing 732 for replenishing reservoir 712 and forward flushing the fritted disc in fritted funnel 718. Stopcock assembly 738 similarly consists of a 3-way valve 740, glass capillary tubing 742 and 746 in the main fluid line, and a section of glass capillary tubing 744 that acts as a drain for the system.

Referring to FIG. 1, assembly 720 consists of a cylinder 754, a cup-like piston indicated by 756 and a weight 758 that fits inside piston 756. Attached to bottom end of cylinder 754 is a No. 400 mesh stainless steel cloth screen 759 that is biaxially stretched to tautness prior to attachment. An absorbent polymer composition indicated generally as 760 rests on screen 759. Cylinder 754 is bored from a transparent Lexan® rod (or equivalent) and has an inner diameter of 6.00 cm (area=28.27 cm$^2$), with a wall thickness of approximately 5 mm and a height of approximately 5 cm. The piston 756 is in the form of a Teflon® or Kel-F® cup and is machined to be a slip fit in cylinder 754 with an annular clearance between the cylinder and the piston of between 0.114 mm and 0.191 mm. Cylindrical stainless steel weight 758 is machined to fit snugly within-piston 756 and is fitted with a handle on the top (not shown) for ease in removing. For a confining pressure of 0.7 psi, the combined weight of piston 756 and weight 758 is 1390 g, which corresponds to a pressure of 0.7 psi for an area of 28.27 cm². For a confining pressure of 1.4 psi, the combined weight of piston 756 and weight 758 is 2780 g.

The components of apparatus 710 are sized such that the flow rate of synthetic urine therethrough, under a 10 cm hydrostatic head, is at least 36 grams per hour per square centimeter of the fritted disc in the fritted funnel 718. Factors particularly impactful on flow rate are the permeability of the fritted disc in fritted funnel 718 and the inner diameters of glass tubing 724, 730, 734, 742, 746 and 731a, and stopcock valves 728 and 740.

Reservoir 712 is positioned on an analytical balance 716 that is accurate to at least 0.01 g with a drift of less than 0.1 g/hr. The balance is preferably interfaced to a computer with software than can (i) monitor balance weight change at pre-set time intervals from the initiation of the PUP test and (ii) be set to auto initiate data acquisition upon a weight change of 0.01–0.05 g, depending on balance sensitivity. Tubing 724 entering the reservoir 712 should not contact either the bottom thereof or cover 714. The volume of fluid (not shown) in reservoir 712 should be sufficient such that air is not drawn into tubing 724 during the measurement. The fluid level in reservoir 712, at the initiation of the measurement, should be approximately 2 mm below the top surface of fritted disc in fritted funnel 718. This can be confirmed by placing a small drop of fluid on the fritted disc and gravimetrically monitoring the flow of this amount of fluid back into reservoir 712. This level should not change significantly when piston/cylinder assembly 720 is positioned within funnel 718. The reservoir should have a sufficiently large diameter (e.g., ~14 cm) so that withdrawal of ~40 mL portions results in a change in the fluid height of less than 3 mm.

Prior to measurement, the assembly is filled with synthetic urine solution and the fritted disc in fritted funnel 718 is flushed so that it is filled with fresh synthetic urine solution. To the extent possible, air bubbles are removed from the bottom surface of the fritted disc and the system that connects the funnel to the reservoir. The following procedures are carried out by sequential operation of the 3-way stopcocks:

1. Excess fluid on the upper surface of the fritted disc is removed (e.g. poured) from fritted funnel 718.
2. The solution height/weight of reservoir 712 is adjusted to the proper level/value.
3. Fritted funnel 718 is positioned at the correct height relative to reservoir 712.
4. Fritted funnel 718 is then covered with fritted funnel cover 722.
5. The reservoir 712 and fritted funnel 718 are equilibrated with valves 728 and 740 of stopcock assemblies 726 and 738 in the open connecting position.
6. Valves 728 and 740 are then closed.
7. Valve 740 is then turned so that the funnel is open to the drain tube 744.
8. The system is allowed to equilibrate in this position for 5 minutes.
9. Valve 740 is then returned to its closed position.

Steps Nos. 7–9 temporarily "dry" the surface of fritted funnel 718 by exposing it to a small hydrostatic suction of ~5 cm. This suction is applied if the open end of tube 744 extends ~5 cm below the level of the fritted disc in fritted funnel 718 and is filled with synthetic urine. Typically ~0.2 g of fluid is drained from the system during this procedure. This procedure prevents premature absorption of synthetic urine when piston/cylinder assembly 720 is positioned within fritted funnel 718. The quantity of fluid that drains from the fritted funnel in this procedure (called the fritted funnel correction weight) is measured by conducting the PUP test (see below) for a time period of 15 minutes without piston/cylinder assembly 720. Essentially all of the fluid drained from the fritted funnel by this procedure is very quickly reabsorbed by the frit when the test is initiated. Thus, it is necessary to subtract this correction weight from weights of fluid removed from the reservoir during the PUP test (see below).

The absorbent polymer composition 760, is dried by suitable procedures, for example by desiccation under high vacuum at an appropriate temperature for a sufficient period of time, so as to reduce the level of moisture and/or other solvents in the sample as much as possible. The final level of residual moisture, as determined by an appropriate technique such as Karl Fischer titration or thermogravimetric analysis, should be less than about 5%, and preferably less than about 3%. Approximately 0.9 g ($W_{ap}$) of the dried absorbent polymer composition 760 (corresponding to a basis weight of 0.032 g/cm²) is added to cylinder 754 and distributed evenly on screen 759. Care is taken to prevent absorbent polymer 760 from adhering to the inside walls of cylinder 754. The piston 756 is slid into cylinder 754 and positioned on top of the absorbent polymer 760, while ensuring that the piston can slide freely within the cylinder. The piston can be turned gently to help distribute the absorbent polymer. The piston/cylinder assembly 720 is placed on top of the frit portion of funnel 718, the weight 758 is slipped into piston 756, and the top of funnel 718 is then covered with fritted funnel cover 722. After the balance reading is checked for stability, the test is initiated by opening valves 728 and 740 so as to connect funnel 718 and reservoir 712. With auto initiation, data collection commences immediately, as funnel 718 begins to reabsorb fluid.

The weight of fluid remaining in the reservoir 712 is recorded at frequent intervals for the duration of the test. The PUP capacity at any given time, t, is calculated as follows:

$$\text{PUP capacity (gm/gm; } t) = [W_r(t=0) - W_r(t) - W_{fc}]/W_{ap}$$

where $W_r(t=0)$ is the weight in grams of reservoir 712 prior to initiation, $W_r(t)$ is the weight in grams of reservoir 712 at the elapsed time t (e.g., 1, 2, 4, 8, or 16 hours), $W_{fc}$ is the fritted funnel correction weight in grams (measured separately), and $W_{ap}$ is the initial dry weight in grams of the absorbent polymer.

2. Ball Burst Strength (BBS) Test

This test determines the ball burst strength (BBS) of an absorbent polymer composition. The BBS is the force (peak load, in grams force) required to rupture a layer of an absorbent polymer composition that is swollen in synthetic urine solution, under procedures specified in the test method. BBS is a measure of the integrity of a layer of the absorbent polymer composition in the swollen state.

Figure 4:
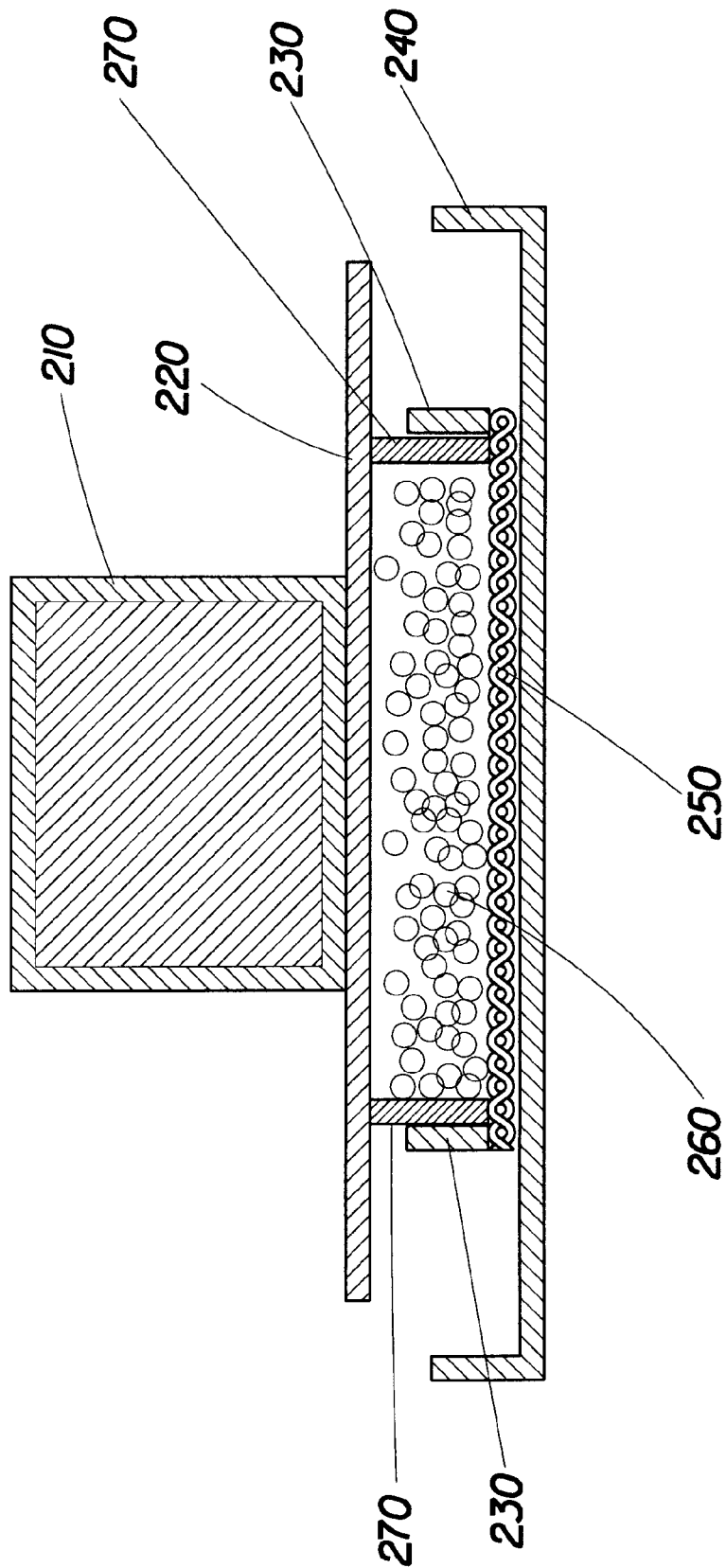
FIG. 4 represents a schematic view of an apparatus for preparing an absorbent polymer composition sample for measurement of the composition's Ball Burst Strength (BBS).

A suitable apparatus for BBS measurement is shown in FIG. 4. This apparatus comprises an inner cylinder 270 which is used to contain an absorbent polymer layer 260, an outer cylinder 230, a Teflon® flat-bottomed tray 240, an inner cylinder cover plate 220, and a stainless steel weight 210. The inner cylinder 270 is bored from a transparent Lexan® rod or equivalent, and has an inner diameter of 6.00 cm (area=28.27 cm$^2$), with a wall thickness of approximately 0.5 cm, and a height of approximately 1.50 cm. The outer-cylinder 230 is bored from a Lexan® rod or equivalent, and has an inner diameter that is slightly larger than the outer diameter of the inner-cylinder 270, so that the inner-cylinder 270 fits within the outer-cylinder 230 and slides freely. The outer cylinder 230 has a wall thickness of approximately 0.5 cm, and a height of approximately 1.00 cm. The bottom of the outside-cylinder 230 is faced with a 400 mesh stainless steel screen 250 that is biaxially stretched to tautness prior to attachment. The inner cylinder cover plate 220 is made of glass plate with a thickness of 0.8 cm and a weight of 500 g. The stainless steel weight 210 has a weight of 1700 g.

Figure 5:
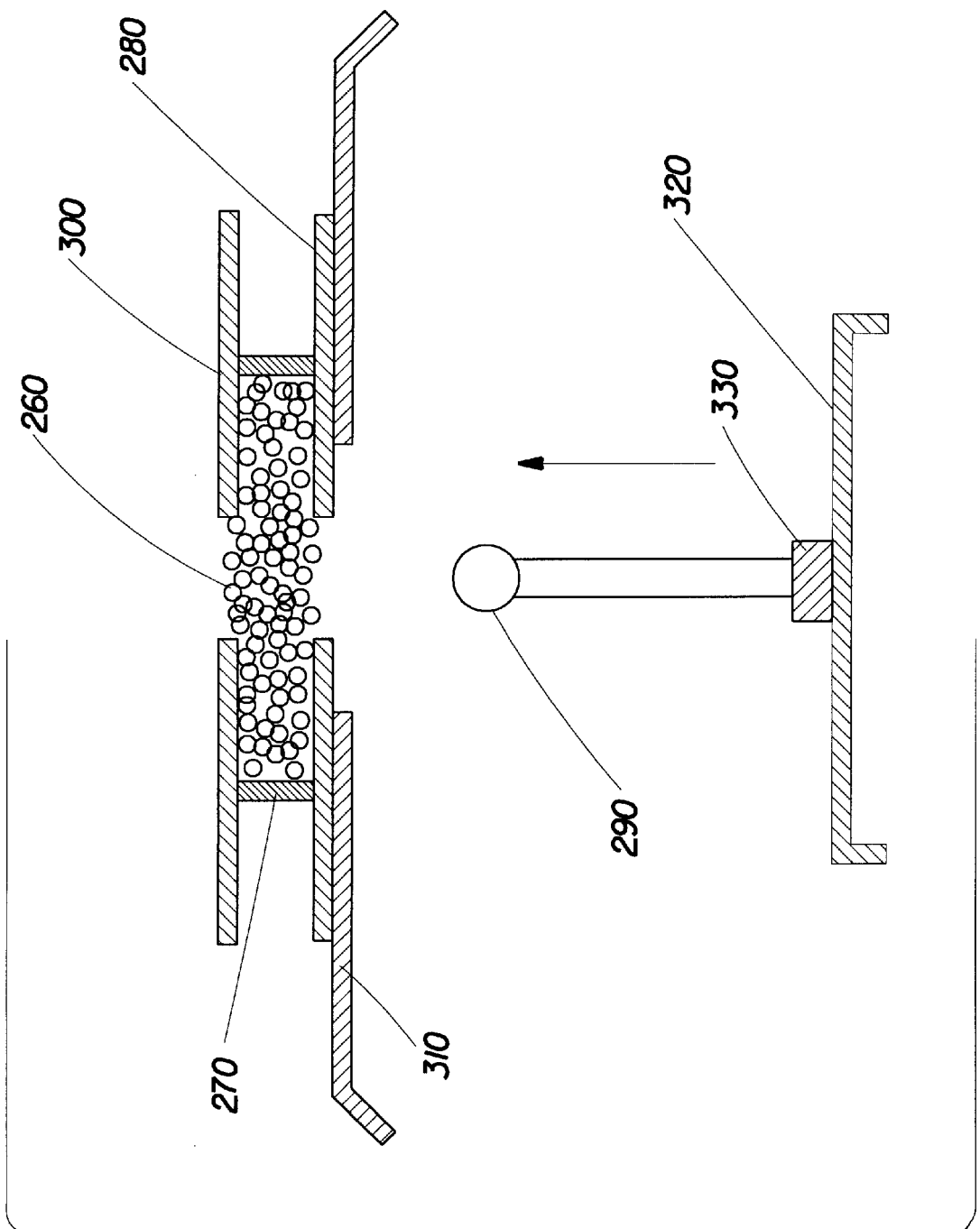
FIG. 5 represents a schematic view of an apparatus for measuring the Ball Burst Strength (BBS) of an absorbent polymer composition.

A Tensile Tester with a burst test load cell (available from Intelect-II-STD Tensile Tester, made by Thwing-Albert Instrument Co., Pennsylvania) is used for this test. Referring to FIG. 5, this instrument comprises a force sensing load cell 330 equipped with a polished stainless steel ball-shaped probe 290, a moving crosshead 320, a stationary crosshead 310, a circular lower platen 280, and an upper clamping platen 300 that is used to clamp the sample 260 pneumatically. The lower clamp platen 280 is mounted on the stationary crosshead 310. Both lower clamp platen 280 and upper clamp platen 300 have a diameter of 115 mm, a thickness of 2.9 mm, and a circular opening 18.65 mm in diameter. The polished stainless steel ball-shaped probe 290 has a diameter of 15.84 mm. During the BBS test procedure, the moving crosshead 320 moves up, causing the probe 290 to contact and penetrate the sample 260. When the probe 290 penetrates the sample 260, the test is considered complete, and the appropriate data are recorded.

Referring to the Sampling Apparatus depicted in FIG. 4, the inner cylinder 270 is inserted into the outside-cylinder 230. A 1.0 g sample of absorbent polymer composition is added to the inner cylinder 270 and dispersed evenly on the 400 mesh stainless steel screen 250. The assembled cylinders with absorbent polymer are transferred to the Teflon® flat-bottomed tray 240, and inner-cylinder cover plate 220 is positioned onto inner-cylinder 270. A 30.0 mL aliquot of synthetic urine solution is poured into the Teflon® flat-bottomed tray 240. The synthetic urine solution passes through the stainless screen and is absorbed by the absorbent polymer composition 260. The stainless weight 210 is placed onto the inner-cylinder cover plate 220 five minutes after addition of the fluid. After an additional 25 minutes, stainless steel weight 210 and inner cylinder cover plate 220 are removed. For the procedure to be valid, all of the synthetic urine solution must be absorbed by the absorbent polymer composition at this point. The inner-cylinder 270 with the layer of swollen absorbent polymer 260 is immediately transferred to the Burst Tester for measurement of the BBS.

Referring to the Burst Tester depicted in FIG. 5, inner-cylinder 270 with the swollen absorbent polymer layer 260 is centrally positioned on lower clamp platen 280 and is fixed pneumatically with upper clamping platen 300. The measurement is performed using a break sensitivity of 10.00 g and a test speed of 5.00 inch/minute. The measurement is initiated and the crosshead 320 moves up until polished stainless steel ball-shaped probe 290 penetrates absorbent material gel layer 260. After a sample burst is registered, moving crosshead 320 returns to start position. The BBS is expressed as peak load in grams force. The average of three determinations is reported as the BBS for the absorbent polymer composition.

D. Absorbent Members

Absorbent members according to the present invention will comprise the previously described absorbent polymer compositions, with or without other optional components such as fibers, thermoplastic material, etc. Preferred materials are described in detail at Col. 23, line 13, through Col. 29, line 16, of U.S. Pat. No. 5,562,646 (Goldman et al.). These absorbent members comprising these absorbent polymers can function as fluid storage members in the absorbent core. The principle function of such fluid storage members is to absorb the discharged body fluid either directly or from other absorbent members (e.g., fluid acquisition/distribution members), and then retain such fluid, even when subjected to pressures normally encountered as a result of the wearer's movements. It should be understood, however, that such polymer-containing absorbent members can serve functions other than fluid storage.

In a preferred embodiment, the absorbent members according to the present invention will contain one or more regions having a relatively high concentration of these absorbent polymers. In order to provide relatively thin absorbent articles capable of absorbing and retaining large quantities of body fluids, it is desirable to maximize the level of these absorbent polymers and to minimize the level of other components, in particular fibrous components. In order to utilize these absorbent polymers at relatively high concentrations, however, it is important that these polymers have a relatively high demand absorbency capacity under a relatively high confining pressure (i.e., PUP capacity) and preferably a relatively high permeability under pressure (i.e., SFC). This is so that the polymer, when swollen in the presence of body fluids, provides adequate capability to acquire these discharged body fluids and then transport these fluids through the zone or layer with relatively high gel concentration to other regions of the absorbent member and/or absorbent core and/or then to store these body fluids.

In measuring the concentration of absorbent polymer composition in a given region of an absorbent member, the percent by weight of the absorbent polymer relative to the combined weight of absorbent polymer and any other components (e.g., fibers, thermoplastic material, etc.) that are present in the region containing the polymer is used. With this in mind, the concentration of the absorbent polymer composition in a given region of an absorbent member of the present invention will preferably be in the range of from about 40 to 100%, from about 50 to 100%, from about 60 to 100%, from about 70 to 100%, from about 80 to 100%, or from about 90% to 100%. Of course, in general, the higher the relative concentration of the absorbent polymer, the thinner and less bulky the absorbent member.

E. Absorbent Cores and Absorbent Articles

The absorbent polymer compositions of the present invention can be used just as conventional absorbent polymers in any absorbent core and/or absorbent article used for the absorption of body fluids, as described in U.S. Pat. No. 5,562,646 (Goldman et al.). The '646 patent describes absorbent cores in detail at Col. 33, line 7, through Col. 52, line 24; and describes absorbent articles in detail at Col. 52, line 25, through Col. 54, line 9. Such articles include diapers, catamenial products and/or adult incontinence products. Substitution of mixed-bed ion-exchange absorbent polymers for the conventional absorbent polymers at the same weight will allow for increased absorbent capacity of the article. Alternatively, the absorbent polymers can be substituted at a lower weight so as not to increase the absorbent capacity of the article, but to allow for a lighter, thinner, and/or less bulky article.

Incorporation of absorbent polymers of the present invention in any previously disclosed absorbent articles is obvious to one skilled in the art. Such products include those with features, for example, such as breathable backsheets, hook-and-loop fasteners, bicomponent fiber matrices, and the like.

Absorbent articles which may contain absorbent polymer compositions described herein are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al.), issued Jul. 12, 1977. More preferred stiffened fibers are disclosed in U.S. Pat. No. 4,822,453 (Dean et al.), issued Apr. 18, 1989; U.S. Pat. No. 4,888,093 (Dean et al.), issued Dec. 19, 1989; U.S. Pat. No. 4,898,642 (Moore et al.), issued Feb. 6, 1990; and U.S. Pat. 5,137,537 (Herrow et al.), issued Aug. 11, 1992; U.S. Pat. No. 4,818,598 (Wong) issued Apr. 4, 1989; U.S. Pat. No. 5,562,646, (Goldman et al.) issued Oct. 8, 1996; U.S. Pat. 5,217,445 (Young et al.), issued Jun. 8, 1993; U.S. Pat. No. 5,360,420, (Cook et al.), issued Nov. 1, 1994; U.S. Pat. No. 4,935,022 (Lash et al.); U.S. applications Ser. No. 08/153,739 (Dragoo et al.), filed Nov. 16, 1993; U.S. application Ser. No. 08/164,049 (Dragoo et al.), filed Dec. 8, 1993; U.S. Pat. No. 4,260,443 (Lindsay et al.); U.S. Pat. No. 4,467,012 (Pedersen et al.), issued Aug. 21, 1984; U.S. Pat. No. 4,715,918 (Lang), issued Dec. 29, 1987; U.S. Pat. No. 4,851,069 (Packard et al.), issued Jul. 25, 1989; U.S. Pat. No. 4,950,264 (Osborn), issued Aug. 21, 1990; U.S. Pat. No. 4,994,037 (Bernardin), issued Feb. 19, 1991; U.S. Pat. No. 5,009,650 (Bernardin), issued Apr. 23, 1991; U.S. Pat. No. 5,009,653 (Osborn), issued Apr. 23, 1991; U.S. Pat. No. 5,128,082 (Makoui), Jul. 7, 1992; U.S. Pat. No. 5,149,335 (Kellenberger et al.), issued Sep. 22, 1992; and U.S. Pat. No. 5,176,668 (Bernardin),issued Jan. 5, 1993; U.S. application Ser. No. 141,156 (Richards et al.), filed Oct. 21, 1993; U.S. Pat. No. 4,429,001 (Kolpin et al.), issued Jan. 31, 1984; U.S. patent application Ser. No. 07/794,745, (Aziz et al.) filed on Nov. 19, 1991; all of which are incorporated by reference.

F. Specific Examples

A lightly crosslinked, partially-neutralized poly(acrylic acid) absorbent polymer with a relatively high PUP capacity (~33 g/g at 0.7 psi; 60 minutes) is obtained from the Chemdal Corporation of Palantine, Ill. (ASAP-2300; lot no. 426152). (Similar samples of ASAP-2300 are available from The Procter & Gamble Co., Paper Technology Division, Cincinnati, Ohio) This material serves as a control sample and is designated herein as "Control Sample".

A sample of an absorbent polymer that provides increased integrity relative to conventional polyacrylate absorbent polymers is obtained from Nippon Shokubai (Lot #TN37408). This is a polyacrylate that is surface-treated with polyethylenimine. The polymer is described in detail in U.S. Pat. No. 5,382,610, filed Jan. 17, 1995. This material is referred to herein as "Sample ST".

EXAMPLE 1

Preparation of Ion-Exchange Absorbent Polymers (i) Cation-Exchange Absorbent Polymer To prepare the cation-exchange absorbent polymer, a portion of the Control Sample is sieved with a U.S.A. Series Standard 50 mesh sieve to remove particles that are larger than about 300 microns in diameter. About 50 grams of the sieved absorbent polymer, with particle size smaller than about 300 microns, is converted to the acid form by suspending the polymer in a dilute hydrochloric acid solution which is prepared by adding about 46.5 g concentrated HCl (Baker; 36.5–38% HCl) to about 900 mL distilled deionized water. The suspension is stirred gently for about 1.5 hours, after which the absorbent polymer is allowed to settle, and the supernatant fluid is removed by decantation. The decanted liquid is replaced by an equal volume of distilled deionized water, the suspension is shaken gently for approximately one hour, the absorbent polymer is allowed to settle, and the supernatant fluid is again removed by decantation. This exchange process is repeated (about eight times) with an equal volume of distilled deionized water until the pH of the supernatant liquid reaches 5–6. The exchange process is then repeated three times with isopropanol (reagent grade; VWR, West Chester, Pa.), three times with acetone (reagent grade; VWR), and once with anhydrous ether (reagent grade; EM Science, Gibbstown, N.J.). The product is spread out gently on a sheet of polytetrafluoroethylene and allowed to dry overnight. After gentle manual disruption with a spatula, the product is dried under high vacuum for 96 hours at room temperature to remove any residual solvents. The sample is sieved through a U.S.A. 20 mesh sieve to remove any large particles or agglomerates. Approximately 30 grams of acid-form, crosslinked poly (acrylic acid), ion-exchange absorbent polymer is obtained and stored under a dry atmosphere (Sample PAA).

(ii) Anion-Exchange Absorbent Polymer

Branched polyethylenimine with a nominal weight average molecular weight of 750,000 g/mole is obtained as a 50% aqueous solution from Aldrich Chemical Co., Milwaukee, Wis. (catalog number 18,917–8; lot number 12922PQ). A 20 gram sample of this solution is further diluted with 37 grams of distilled water and is stirred for 30 minutes in a 250 mL beaker to achieve complete dissolution. Ethylene glycol diglycidyl ether (50% soln.), 2.14 grams (Aldrich Chemical Co., catalog number, E2,720-3; lot number, 07405DN), is added to the polyethylenimine solution and the mixture is stirred at room temperature for approximately two minutes before being placed in a vented oven at approximately 65° C. for three hours. The resultant gel is allowed to cool and then broken into pieces approximately 1 to 5 mm in diameter. The mixture is then transferred to a 4000 mL beaker containing two litres of distilled water and stirred gently overnight. The excess water is decanted off and the remaining sample is dried under high vacuum for approximately 96 hours to yield a lightly crosslinked polyethylenimine anion-exchange absorbent polymer which is stored under a dry atmosphere (Sample BPEI).

(iii) Mixed-Bed Ion-Exchange Absorbent Polymer

The crosslinked polyethylenimine anion-exchange absorbent polymer (Sample BPEI) is cryogenically ground and sieved under an atmosphere of dry nitrogen. A particle size fraction is collected which passes through a U.S.A. Series Standard 25 mesh sieve, but not through a U.S.A. Series Standard 70 mesh sieve (i.e. a fraction with particles in the range of approximately 200 to 700 microns in diameter).

Approximately equal weights of the sieved crosslinked poly(acrylic acid) cation-exchange absorbent polymer (Sample PAA) and the sieved crosslinked polyethylenimine anion-exchange absorbent polymer (Sample BPEI) are mixed together so as to distribute the particles of each type of polymer evenly throughout the mixture. This mixture comprises a mixed-bed ion-exchange absorbent polymer composition (Sample MB-1) of the present invention.

(iv) PUP Capacity Measurements

Figure 3:
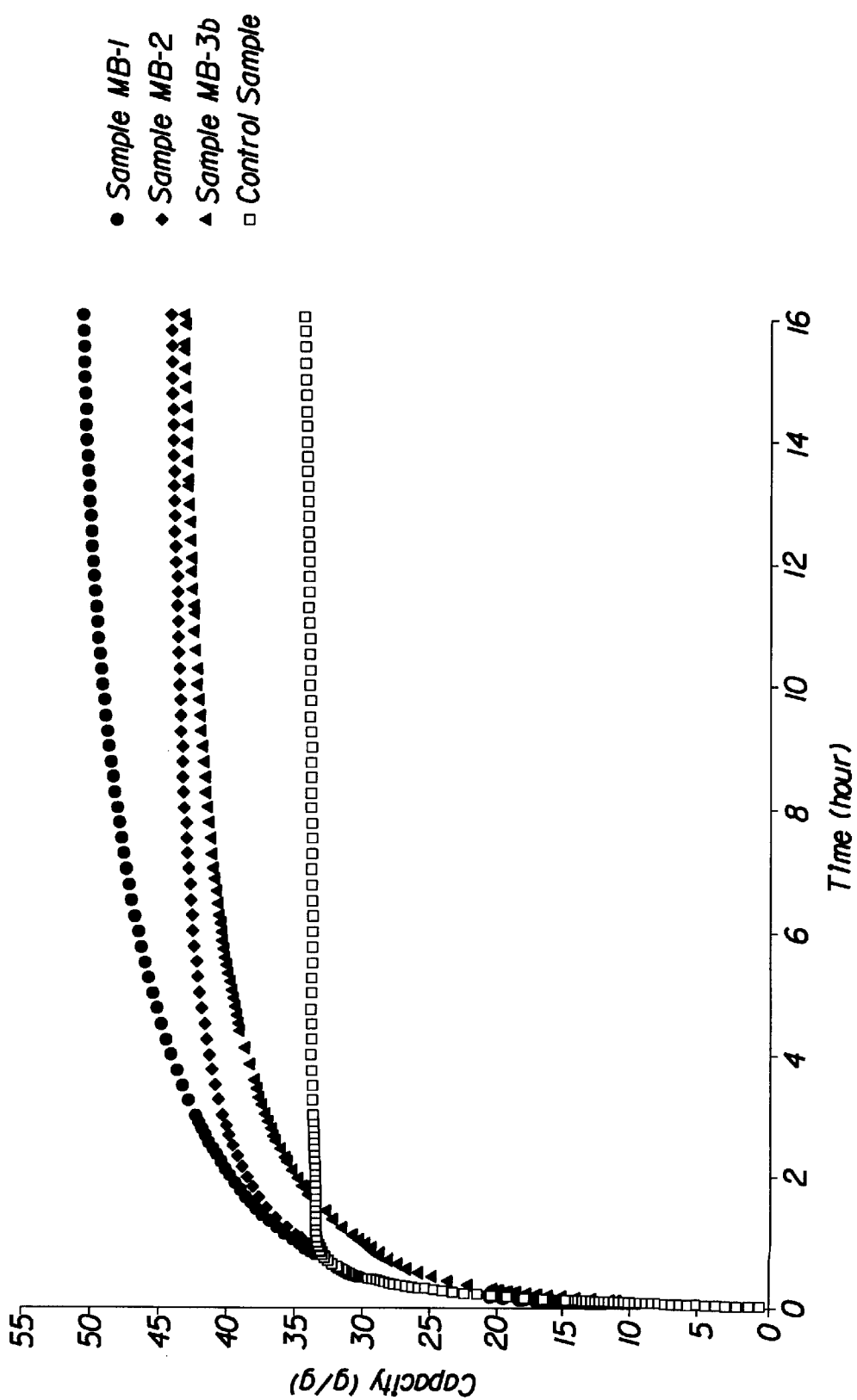
FIG. 3 graphically depicts PUP capacity data for absorbent polymer compositions of the present invention and the prior art, where PUP capacity is measured under a confining pressure of 0.7 psi.

Approximately 0.9 grams of the mixed bed ion-exchange absorbent polymer composition (Sample MB-1) is transferred to a PUP cylinder (as described in the Test Methods section above), and gently spread out over the entire area of the screen comprising the base of the cylinder. PUP capacities are determined on separate samples under confining pressures of 0.7 and 1.4 psi, with the amount of fluid absorbed measured at frequent intervals for a period of 16 hours. The measured PUP capacities at 0.7 psi are shown as a function of time in FIG. 3. Selected PUP capacity data at 2, 4, 8 and 16 hours are listed in Table 1 below.

TABLE 1

PUP Capacities for Absorbent Polymer Compositions

|  | 0.7 psi (4 hrs) | 0.7 psi (8 hrs) | 0.7 psi (16 hrs) | 1.4 psi (2 hrs) | 1.4 psi (8 hrs) | 1.4 psi (16 hrs) |
| --- | --- | --- | --- | --- | --- | --- |
| Sample MB-1 | 44 g/g | 48 g/g | 50 g/g | 32 g/g | 40 g/g | 42 g/g |
| Control Sample | 33 g/g | 33 g/g | 33 g/g | 20 g/g | 20 g/g | 20 g/g |

A comparison of the PUP capacities indicates that the mixed-bed ion-exchange absorbent polymer composition (Sample MB-1) exhibits an approximately 100% increase in PUP capacity at a confining pressure of 1.4 psi, and an approximately 40% increase in PUP capacity at a confining pressure of 0.7 psi after 8 hours, relative to the capacities of the partially neutralized polyacrylate absorbent polymer under analogous test conditions (Control Sample).

(v) Permeability Measurement

A measure of permeability and an indication of porosity is provided by the saline flow conductivity of the gel bed as described in U.S. Pat. No. 5,562,646, (Goldman et al.) issued Oct. 8, 1996. This method is modified for mixed-bed ion-exchange absorbent polymer systems, as discussed below. Approximately 0.9 grams of the mixed-bed ion-exchange absorbent polymer composition (Sample MB-1) is transferred to a cylinder designed for Saline Flow Conductivity measurement (SFC), and is gently spread out over the entire area of the screen comprising the base of the cylinder. The measured saline flow conductivity values are listed in Table 2 below.

TABLE 2

SFC Values for Absorbent Polymer Compositions

|  | SFC Value |
| --- | --- |
| Sample MB-1 | ~68 × $10^{-7}$ cm$^3$ · sec/g |
| Control Sample | ~10 × $10^{-7}$ cm$^3$ · sec/g |

Comparison of the saline flow conductivity values demonstrate that the porosity and permeability of the mixed-bed ion-exchange absorbent polymer composition (Sample MB-1) are substantially greater than those of the partially neutralized polyacrylate absorbent polymer (Control Sample) under analogous test conditions. It is believed that the mixed-bed ion-exchange absorbent polymer sample continues to exchange ions from the saline solution during the SFC measurement. Ultimately, the ion-exchange capacity of the absorbent polymer is exceeded, and the ionic strength of the solution surrounding the swollen polymer increases, resulting in some deswelling of the gel bed. The amount of fluid that is expressed from the gel as a result of this deswelling is small compared to the amount of fluid which flows through the gel bed during the SFC measurement. Because the final thickness of the gel bed is significantly less than the initial thickness, the final thickness of the gel bed is used to calculate SFC values. Using the final thickness of the gel bed in the calculation provides the minimum SFC attained during the measurement. Using the initial or an intermediate thickness of the gel bed will provide even higher SFC values.

Although SFC is not a direct measure of porosity, high permeability to fluid also generally requires a high degree of porosity in particulate absorbent polymer systems. Thus, the relatively high SFC value for the mixed-bed ion-exchange absorbent polymer composition also denotes a relatively high level of porosity.

(vi) Integrity of the Gel Bed

A measure of the integrity of a layer of the absorbent polymer composition in the swollen state is provided by ball burst strength (BBS) as described previously. The measured ball burst strength values for Sample MB-1, Sample ST, and Control Sample are listed in Table 3 below:

TABLE 3

BBS Values for Mixed-bed Ion-exchange Absorbent Polymer Compositions

|  | BBS |
| --- | --- |
| Sample MB-1 | 225 gf |
| Sample ST | 133 gf |
| Control Sample | 17 gf |

A comparison of the ball burst strength values in Table 3 indicate that the mixed-bed ion-exchange absorbent polymer composition (Sample MB-1) exhibits a substantial increase in the integrity of the gel layer relative to the partially neutralized polyacrylate absorbent polymer (Control Sample) and Sample ST under analogous test conditions.

EXAMPLE 2

Preparation of Ion-Exchange Absorbent Polymers (i) Cation-Exchange Absorbent Polymer The cation exchange absorbent polymer is prepared as described in Example 1, Section (i); (Sample PAA).

(ii) Anion-Exchange Absorbent Polymer a) Preparation of Crosslinked Polyallylamine Polyallylamine hydrochloride with a nominal weight average molecular weight of 60,000 g/mole is obtained from Polysciences, Inc. Warrington, Pa. (catalog number 18378; lot number 455913). A solution of polyallylamine hydrochloride is prepared by dissolving 16.4 grams of the polymer in 165 mL distilled water. 15.6 grams of a 50% aqueous sodium hydroxide solution are added dropwise to this solution while stirring. Ethylene glycol diglycidyl ether (50% soln.), 2.0 grams (Aldrich Chemical Co., catalog number, E2,720-3; lot number, 07405DN), is added to the polyallylamine solution and the mixture is stirred at room temperature for approximately two minutes before being placed in a vented oven at approximately 65° C. for three hours. The resultant gel is broken into pieces approximately 5 mm in diameter, and transferred to a 4000 mL beaker containing one litre of distilled water. The mixture is stirred gently overnight and the excess water is decanted off. The remaining sample is dried under high vacuum at room temperature for approximately 96 hours to yield a lightly crosslinked polyallylamine anion-exchange absorbent polymer which is stored under a dry atmosphere (Sample PAAM).

b) Methylation of Sample PAAM

Formic acid (96% soln.), 21.02 grams (Aldrich Chemical Co., catalog number 25,136-4), and formaldehyde (37% soln.), 35.56 grams (Aldrich Chemical Co., catalog number 25,254-9; lot number, 04717TZ), are added to 800 grams of distilled water. Ten grams of crosslinked polyallylamine (Sample PAAM) are added to the above solution and the mixture is placed in an oven at 70° C. for 24 hours. The gel is recovered by decantation, and stirred overnight in 1000 mL water to remove extractables. The supernatant solution is decanted off and replaced with 1 litre of 1.7% aqueous sodium hydroxide solution to remove excess formic acid in the gel. The mixture is allowed to stand for approximately 24 hours and the polymer is recovered by decantation of the supernatant fluid. This process is repeated (about three times) with 1 litre of 1.7% aqueous sodium hydroxide solution until a pH of 13 is obtained. The gel is recovered by vacuum filtration and soaked in 3000 mL of water overnight. The excess water is decanted off and the remaining sample is dried under high vacuum at room temperature for approximately 96 hours to yield a lightly crosslinked tertiary-polyallylamine anion-exchange absorbent polymer which is stored under a dry atmosphere. NMR spectroscopic analysis of the product indicates that approximately 90 percent of the amine groups in the polymer are methylated to form tertiary amine moieties (Sample t-PAAM).

(iii) Mixed-Bed Ion-Exchange Absorbent Polymer

The crosslinked tertiary-polyallylamine anion-exchange absorbent polymer (Sample t-PAAM) is cryogenically ground and sieved under an atmosphere of dry nitrogen. A particle size fraction is collected which passes through a U.S.A. Series Standard 25 mesh sieve, but not through a U.S.A. Series Standard 70 mesh sieve (i.e. a fraction with particles in the range of approximately 200 to 700 microns in diameter).

Approximately 0.29 grams of the sieved crosslinked poly(acrylic acid) cation-exchange absorbent polymer (Sample PAA) and 0.71 grams of the sieved crosslinked tertiary-polyallylamine anion-exchange absorbent polymer (Sample t-PAAM) are mixed together so as to distribute the particles of each type of polymer evenly throughout the mixture. This mixture comprises a mixed-bed ion-exchange absorbent polymer composition (Sample MB-2 of the present invention).

(iv) PUP Capacity Measurements

Approximately 0.9 grams of the mixed bed ion-exchange absorbent polymer composition (Sample MB-2) is transferred to a PUP cylinder (as described in the Test Methods section above), and gently spread out over the entire area of the screen comprising the base of the cylinder. PUP capacities are determined on separate samples under confining pressures of 0.7 and 1.4 psi, with the amount of fluid absorbed measured at frequent intervals for a period of 16 hours. The measured PUP capacities at 0.7 psi are shown as a function of time in FIG. 3. Selected PUP capacity data at 2, 4, 8 and 16 hours are listed in Table 4 below.

TABLE 4

PUP Capacities for Absorbent Polymer Compositions

|  | 0.7 psi (4 hrs) | 0.7 psi (8 hrs) | 0.7 psi (16 hrs) | 1.4 psi (2 hrs) | 1.4 psi (8 hrs) | 1.4 psi (16 hrs) |
|---|---|---|---|---|---|---|
| Sample MB-2 | 41 g/g | 43 g/g | 44 g/g | 33 g/g | 40 g/g | 42 g/g |
| Control Sample | 33 g/g | 33 g/g | 33 g/g | 20 g/g | 20 g/g | 20 g/g |

A comparison of the PUP capacities indicates that the mixed-bed ion-exchange absorbent polymer composition (Sample MB-2) absorbs substantially more synthetic urine solution than the partially neutralized polyacrylate absorbent polymer (Control Sample) under the test conditions described above.

EXAMPLE 3

Preparation of Ion-Exchange Absorbent Polymers (i) Cation-Exchange Absorbent Polymer The cation exchange absorbent polymer is prepared as described in Example 1 Section (i); (Sample PAA).

(ii) Anion-Exchange Absorbent Polymer a) Preparation of Linear Polyethylenimine

Poly(2-ethyl-2-oxazoline) with a nominal weight average molecular weight of 500,000 g/mole is obtained from Aldrich Chemical Co., Milwaukee, Wis. (catalog number 37, 397-4; lot number 17223HG). A 100 gram sample of poly (2-ethyl-2-oxazoline) is dissolved in a hydrochloric acid solution which is prepared by mixing 1000 mL water and 200 mL concentrated hydrochloric acid. The solution is refluxed at 100° C. for 72 hours then allowed to cool to room temperature. Product is precipitated from the reaction solution by adding 256 mL of a 50% solution of sodium hydroxide dropwise while stirring. The white solid precipitate is recovered by vacuum filtration and washed with 5000 mL of water. The product is freeze dried for 48 hours to yield linear polyethylenimine.

b) Preparation of Crosslinked Linear Polyethylenimine

Linear polyethylenimine, 5.0 g, as prepared above, is dissolved in 50 mL of methanol. Ethylene glycol diglycidyl ether (50% soln.), 0.5 grams (Aldrich Chemical Co., catalog number E2,720-3; lot number, 07405DN), is added to the linear polyethylenimine solution and the mixture is stirred at room temperature for approximately two minutes before being placed in a vented oven at approximately 65° C. for three hours. The resultant gel is broken into particles approximately 5 mm in diameter, and is stirred gently in 500 mL of methanol overnight. The sample is recovered by decantation, and is dried under high vacuum for approximately 48 hours to yield a lightly crosslinked polyethylenimine anion-exchange absorbent polymer which is stored under a dry atmosphere (Sample LPEI-1)

c) Partial Methylation of Crosslinked Polyethylenimine

Linear polyethylenimine, 5.37 g, as prepared above, is dissolved in 45 grams of methanol. Ethylene glycol diglycidyl ether (50% soln.), 1.07 grams (Aldrich Chemical Co., catalog number E2,720-3; lot number, 07405DN), is added to the linear polyethylenimine solution and the mixture is stirred at room temperature for approximately two minutes before being placed in a vented oven at approximately 65° C. for three hours. The resultant gel is broken into particles approximately 5 mm in diameter, and is stirred gently in 500 mL of methanol overnight. The sample is recovered by decantation, and is dried under high vacuum for approximately 48 hours to yield a lightly crosslinked polyethylenimine anion-exchange absorbent polymer which is stored under a dry atmosphere (Sample LPEI-2).

Formic acid (96% soln.), 48.44 grams (Aldrich Chemical Co., catalog number 25,136-4), and formaldehyde (37% soln.), 81.17 grams (Aldrich Chemical Co., catalog number 25,254-9), are added to 370.39 grams of distilled water to yield 500 grams of stock solution. 46.98 grams of this stock solution are added to 5.37 grams of crosslinked linear polyethylenimine (Sample LPEI-2). The mixture is further diluted with 450 mL of distilled water and placed in an oven at 70° C. for 24 hours. The gel is recovered by decantation, and stirred overnight in 2500 mL water to remove extractables. The supernatant solution is decanted off and replaced with 20 mL of 50% aqueous sodium hydroxide solution to remove excess formic acid in the gel. The mixture is allowed to stand for approximately 3 hours and the polymer is recovered by decanting the supernatant fluid. This process is repeated (about three times) with 20 mL of 50% aqueous sodium hydroxide solution until a pH of 13 is obtained. The gel is recovered by vacuum filtration and soaked in 1000 mL of water overnight. The supernatant fluid is decanted off and replaced with 500 mL of tetrahydrofuran. After 24 hours, the tetrahydrofuran is decanted off and replaced by 500 mL of anhydrous ether. After 24 hours, the ether is decanted off and the gel is dried under high vacuum at room temperature for 48 hours. NMR spectroscopic analysis of the product indicates that approximately 65 percent of the amine groups in the polymer are methylated to form tertiary amine moieties. (Sample NMEI-65)

(iii) Mixed-Bed Ion-Exchange Absorbent Polymer

The crosslinked linear polyethylenimine and poly(N-methylethylenimine) anion-exchange absorbent polymers (Samples LPEI-1 and NMEI-65) are each separately cryogenically ground and sieved under an atmosphere of dry nitrogen. For each material, a particle size fraction is collected which passes through a U.S.A. Series Standard 25 mesh sieve, but not through a U.S.A. Series Standard 70 mesh sieve (i.e. a fraction with particles in the range of approximately 200 to 700 microns in diameter).

Approximately one gram of each of the sieved crosslinked anion-exchange absorbent polymers (Samples LPEI-1 and NMEI-65) are separately mixed with one gram portions of the sieved crosslinked poly(acrylic acid) cation-exchange absorbent polymer (Sample PAA) so as to distribute the particles of each type of polymer evenly throughout the mixtures. These mixtures each comprise a mixed-bed ion-exchange absorbent polymer composition (Samples MB-3a and MB-3b, respectively) of the present invention.

(iv) PUP Capacity Measurements

Approximately 0.9 grams of the mixed bed ion-exchange absorbent polymer compositions (Sample MB-3a, and MB-3b) are transferred to separate PUP cylinders (as described in the Test Methods section above), and gently spread out over the entire area of the screen comprising the base of the cylinder. PUP capacities are determined on separate samples under confining pressures of 0.7 and 1.4 psi, with the amount of fluid absorbed measured at frequent intervals for a period of 16 hours. The measured PUP capacities at 0.7 psi are shown as a function of time in FIG. 3. Selected PUP capacity data at 4, 8 and 16 hours are listed in Table 5 below.

TABLE 5

PUP Capacities for Absorbent Polymer Compositions

|  | 0.7 psi (4 hrs) | 0.7 psi (8 hrs) | 0.7 psi (16 hrs) | 1.4 psi (8 hrs) | 1.4 psi (16 hrs) |
|---|---|---|---|---|---|
| Sample MB-3a | — | — | — | 32 | 37 |
| Sample MB-3b | 39 g/g | 42 g/g | 43 g/g | — | — |
| Control Sample | 33 g/g | 33 g/g | 33 g/g | 20 g/g | 20 g/g |

A comparison of the PUP capacities indicates that the mixed-bed ion-exchange absorbent polymer compositions (Sample MB-3a and MB-3b) absorb substantially more synthetic urine solution than the partially neutralized polyacrylate absorbent polymer (Control Sample) under the test conditions described above.

What is claimed is:

1. An absorbent polymer composition, said polymer composition consisting essentially of absorbent polymers, each of said polymers being capable of absorbing at least 10 times its weight in deionized water, allowing for adjustment of the pH of the system, wherein said polymer composition has a Performance Under Pressure (PUP) capacity in synthetic urine solution of at least about 39 g/g under a confining pressure of 0.7 psi after 4 hours, and a Ball Burst Strength (BBS) value of at least about 50 gf.

2. The absorbent polymer composition of claim 1 having a PUP capacity of at least about 41 g/g under a confining pressure of 0.7 psi after 4 hours.

3. The absorbent polymer composition of claim 2 having a PUP capacity of at least about 43 g/g under a confining pressure of 0.7 psi after 4 hours.

4. The absorbent polymer composition of claim 3 having a PUP capacity of at least about 44 g/g under a confining pressure of 0.7 psi after 4 hours.

5. The absorbent polymer composition of claim 1 having a PUP capacity of from about 39 g/g to about 58 g/g under a confining pressure of 0.7 psi after 4 hours.

6. The absorbent polymer composition of claim 5 having a PUP capacity of from about 41 g/g to about 55 g/g under a confining pressure of 0.7 psi after 4 hours.

7. The absorbent polymer composition of claim 6 having a PUP capacity of from about 43 g/g to about 50 g/g, under a confining pressure of 0.7 psi after 4 hours.

8. The absorbent polymer composition of claim 1 having a BBS value of at least about 100 gf.

9. The absorbent polymer composition of claim 8 having a BBS value of at least about 150 gf.

10. An absorbent polymer composition, said polymer composition consisting essentially of absorbent polymers, each of said polymers being capable of absorbing at least 10 times its weight in deionized water, allowing for adjustment of the pH of the system, wherein said polymer composition has a PUP capacity in synthetic urine solution of at least about 36 g/g under a confining pressure of 0.7 psi after 4 hours, and a BBS value of at least about 100 gf.

11. The absorbent polymer composition of claim 10 having a PUP capacity of at least about 38 g/g under a confining pressure of 0.7 psi after 4 hours.

12. The absorbent polymer composition of claim 11 having a PUP capacity of at least about 40 g/g under a confining pressure of 0.7 psi after 4 hours.

13. The absorbent polymer composition of claim 12 having a PUP capacity of at least about 42 g/g under a confining pressure of 0.7 psi after 4 hours.

14. The absorbent polymer composition of claim 10 having a PUP capacity of from about 36 g/g to about 58 g/g under a confining pressure of 0.7 psi after 4 hours.

15. The absorbent polymer composition of claim 14 having a PUP capacity of from about 38 g/g to about 55 g/g under a confining pressure of 0.7 psi after 4 hours.

16. The absorbent polymer composition of claim 15 having a PUP capacity of from about 40 g/g to about 50 g/g, under a confining pressure of 0.7 psi after 4 hours.

17. The absorbent polymer composition of claim 10 having a BBS value of at least about 150 gf.

18. The absorbent polymer composition of claim 17 having a BBS value of at least about 200 gf.

19. An absorbent polymer composition, said polymer composition consisting essentially of absorbent polymers, each of said polymers being capable of absorbing at least 10 times its weight in deionized water, allowing for adjustment of the pH of the system, wherein said polymer composition has a PUP capacity in synthetic urine solution of at least about 33 g/g under a confining pressure of 0.7 psi after 4 hours, and a BBS value of at least about 150 gf.

20. The absorbent polymer composition of claim 19 having a PUP capacity of at least about 35 g/g under a confining pressure of 0.7 psi after 4 hours.

21. The absorbent polymer composition of claim 20 having a PUP capacity of at least about 37 g/g under a confining pressure of 0.7 psi after 4 hours.

22. The absorbent polymer composition of claim 21 having a PUP capacity of at least about 40 g/g under a confining pressure of 0.7 psi after 4 hours.

23. The absorbent polymer composition of claim 19 having a PUP capacity of from about 33 g/g to about 58 g/g under a confining pressure of 0.7 psi after 4 hours.

24. The absorbent polymer composition of claim 23 having a PUP capacity of from about 35 g/g to about 55 g/g under a confining pressure of 0.7 psi after 4 hours.

25. The absorbent polymer composition of claim 24 having a PUP capacity of from about 37 g/g to about 50 g/g, under a confining pressure of 0.7 psi after 4 hours.

26. The absorbent polymer composition of claim 19 having a BBS value of at least about 200 gf.

27. An absorbent polymer composition, said polymer composition consisting essentially of absorbent polymers, each of said polymers being capable of absorbing at least 10 times its weight in deionized water, allowing for adjustment of the pH of the system, wherein said polymer composition has a PUP capacity in synthetic urine solution of at least about 30 g/g under a confining pressure of 0.7 psi after 4 hours, and a BBS value of at least about 200 gf.

28. The absorbent polymer composition of claim 27 having a PUP capacity of at least about 32 g/g under a confining pressure of 0.7 psi after 4 hours.

29. The absorbent polymer composition of claim 28 having a PUP capacity of at least about 34 g/g under a confining pressure of 0.7 psi after 4 hours.

30. The absorbent polymer composition of claim 29 having a PUP capacity of at least about 37 g/g under a confining pressure of 0.7 psi after 4 hours.

31. The absorbent polymer composition of claim 27 having a PUP capacity of from about 30 g/g to about 58 g/g under a confining pressure of 0.7 psi after 4 hours.

32. The absorbent polymer composition of claim 31 having a PUP capacity of from about 32 g/g to about 55 g/g under a confining pressure of 0.7 psi after 4 hours.

33. The absorbent polymer composition of claim 32 having a PUP capacity of from about 34 g/g to about 50 g/g, under a confining pressure of 0.7 psi after 4 hours.

34. An absorbent member for the containment of aqueous body fluids, which comprises at least one region comprising the absorbent polymer composition of claim 1.

35. An absorbent member for the containment of aqueous body fluids, which comprises at least one region comprising the absorbent polymer composition of claim 10.

36. An absorbent member for the containment of aqueous body fluids, which comprises at least one region comprising the absorbent polymer composition of claim 19.

37. An absorbent member for the containment of aqueous body fluids, which comprises at least one region comprising the absorbent polymer composition of claim 27.

38. An absorbent article comprising a liquid pervious topsheet, a backsheet and an absorbent core positioned between the topsheet and the backsheet, wherein the absorbent core comprises the absorbent member of claim 34.

39. An absorbent article comprising a liquid pervious topsheet, a backsheet and an absorbent core positioned between the topsheet and the backsheet, wherein the absorbent core comprises the absorbent member of claim 35.

40. An absorbent article comprising a liquid pervious topsheet, a backsheet and an absorbent core positioned between the topsheet and the backsheet, wherein the absorbent core comprises the absorbent member of claim 36.

41. An absorbent article comprising a liquid pervious topsheet, a backsheet and an absorbent core positioned between the topsheet and the backsheet, wherein the absorbent core comprises the absorbent member of claim 37.

* * * * *

UNITED STATES PATENT AND TRADEMARK OFFICE
CERTIFICATE OF CORRECTION

PATENT NO.    : 6,121,509
DATED         : September 19, 2000
INVENTOR(S)   : Ashraf et al.

Page 1 of 1

It is certified that error appears in the above-identified patent and that said Letters Patent is hereby corrected as shown below:

<u>Column 3,</u>
Line 58, please delete "afier" and insert therefor -- after --.

<u>Column 7,</u>
Line 15, please delete "β-chlorocinnamic" and insert therefor -- p-chlorocinnamic --.

Signed and Sealed this

Twenty-sixth Day of November, 2002

Attest:

Attesting Officer

JAMES E. ROGAN
*Director of the United States Patent and Trademark Office*